(12) United States Patent
Hollenbach et al.

(10) Patent No.: US 9,734,389 B2
(45) Date of Patent: Aug. 15, 2017

(54) SYSTEM WITH MULTI-AXIS ATHLETIC PERFORMANCE TRACKING

(71) Applicant: Under Armour, Inc., Baltimore, MD (US)

(72) Inventors: Samuel J. Hollenbach, Baltimore, MD (US); Mark A. Oleson, Baltimore, MD (US); Erik Damen, Doorwerth (NL); Richard Mayerhofer, Munich (DE)

(73) Assignee: Under Armour, Inc., Baltimore, MD (US)

( * ) Notice: Subject to any disclaimer, the term of this patent is extended or adjusted under 35 U.S.C. 154(b) by 293 days.

(21) Appl. No.: 14/593,219

(22) Filed: Jan. 9, 2015

(65) Prior Publication Data

US 2015/0202494 A1 Jul. 23, 2015

Related U.S. Application Data

(60) Provisional application No. 61/925,335, filed on Jan. 9, 2014.

(51) Int. Cl.
*A63F 13/12* (2006.01)
*G06K 9/00* (2006.01)
*A61B 5/11* (2006.01)
*A61B 5/00* (2006.01)

(52) U.S. Cl.
CPC ........ *G06K 9/00342* (2013.01); *A61B 5/1116* (2013.01); *A61B 5/1118* (2013.01); *A61B 5/7285* (2013.01); *A61B 5/6805* (2013.01); *A61B 2503/10* (2013.01); *A61B 2560/029* (2013.01); *A61B 2562/0219* (2013.01)

(58) Field of Classification Search
CPC ....................................................... A63F 13/12
See application file for complete search history.

(56) References Cited

U.S. PATENT DOCUMENTS

| | | | |
|---|---|---|---|
| 2004/0010390 A1* | 1/2004 | Kelly, Jr. ............. | A61B 5/0002 702/150 |
| 2010/0279825 A1 | 11/2010 | Riley et al. | |
| 2012/0253485 A1 | 10/2012 | Weast et al. | |
| 2013/0190903 A1* | 7/2013 | Balakrishnan ....... | A61B 5/7246 700/91 |

OTHER PUBLICATIONS

International Search Report, PCT US2015/010782, mailed Apr. 9, 2015.

\* cited by examiner

*Primary Examiner* — Omkar Deodhar

(57) ABSTRACT

Techniques are described for calculating athletic performance during an athletic activity. In one embodiment, a processor of a sensing device comprising one or more sensors measures an activity parameter of a user. The processor analyzes the activity parameter to determine whether the activity parameter meets a predetermined criteria. When the activity parameter meets the predetermined criteria, the processor arms the one or more sensors. The arming comprises activating the one or more sensors to collect exercise data for a known exercise activity performed by the user. In another embodiment, the processor of the sensing device comprising one or more sensors arms the one or more sensors to collect data when the activity parameter of the user meets a predetermined criteria. After arming the one or more sensors, the processor collects exercise data for a known exercise activity performed by the user.

21 Claims, 6 Drawing Sheets

500

510

Arming the one or more sensors to collect data when an activity parameter of a user meets a predetermined criteria

515

Collecting exercise data for a known exercise activity performed by the user

FIG.5

SYSTEM WITH MULTI-AXIS ATHLETIC PERFORMANCE TRACKING

CROSS-REFERENCE TO RELATED APPLICATIONS

This application claims priority to U.S. provisional patent application No. 61/925,335 filed Jan. 9, 2014, the entirety of which is incorporated by reference herein.

TECHNICAL FIELD

The present disclosure relates to techniques for calculating athletic performance of an athlete during an athletic activity.

BACKGROUND

Speed, agility, reaction time, and power are some of the determining characteristics influencing the athleticism of an athlete. Athletes strive to improve their athletic performance in these areas, and coaches, recruiters and athletic teams seek athletes having the best set of these characteristics for a particular sport. Conventional systems often utilize Global Positioning System (GPS) devices to track the distance travel by an athlete over a predetermined period of time. These GPS devices often extrapolate average speed from these distance and time measurements. These systems, however, often fail to compensate for errors introduced into the extrapolation caused by the earth's rotation and/or the angular position of the runner relative to the ground.

BRIEF DESCRIPTION OF THE DRAWINGS

FIG. 5 is a flow diagram of the sensing device collecting exercise data for a user.

Like reference numerals have been used to identify like elements throughout this disclosure.

DESCRIPTION OF EXAMPLE EMBODIMENTS

Overview

Figure 1:
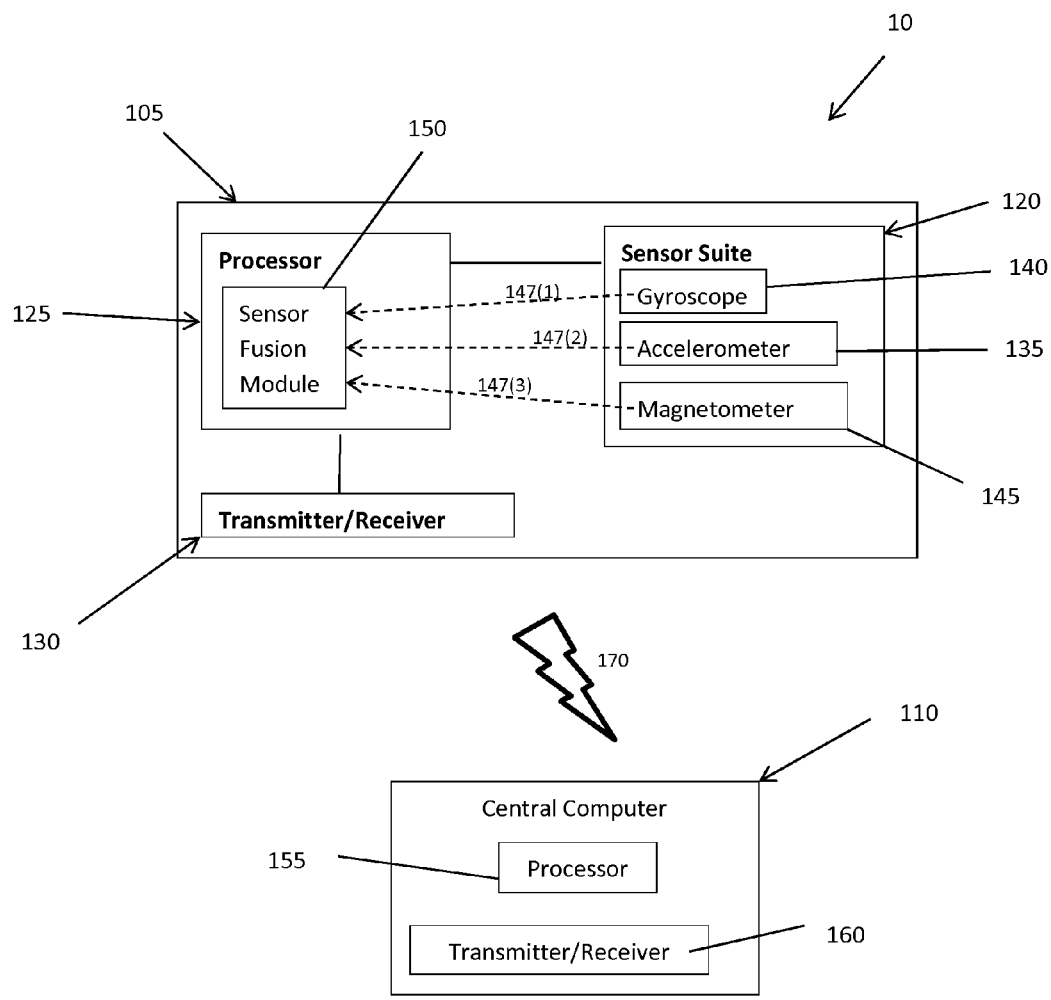
FIG. 1 is block diagram of a system for calculating athletic performance in accordance with an embodiment of the invention.

Techniques are described herein for calculating athletic performance during an athletic activity. In one embodiment, a processor of a sensing device comprising one or more sensors measures an activity parameter of a user. The processor analyzes the activity parameter to determine whether the activity parameter has characteristics that meet a predetermined criterion or predetermined criteria. When the activity parameter has characteristics that meet the predetermined criteria, the processor arms the one or more sensors. The arming comprises activating the one or more sensors to collect exercise data for a known exercise activity performed by the user.

In another embodiment, the processor of the sensing device comprising one or more sensors arms the one or more sensors to collect data when the activity parameter of the user meets a predetermined criterion or predetermined criteria. After arming the one or more sensors, the processor collects exercise data for a known exercise activity performed by the user.

Example Embodiments

The present disclosure relates to techniques for collecting and calculating performance data during an athletic activity. For example, techniques are described herein for arming a system of one or more sensors worn by or coupled to an athlete, collecting exercise data from the athlete and classifying the collected exercise data as data that is associated with a known exercise activity performed by the user. Upon collecting the exercise data, a processor or controller may analyze the data to determine parameters performed by the athlete during the known exercise activity. The techniques described herein enable electronic devices (e.g., sensing devices) to determine when sensors are in an armed state and to collect data for a known exercise activity after the sensors are in the armed state, thus improving the functioning of the electronic devices. Additionally, the electronic devices can more efficiently collect and process data for the known exercise activity.

For example, as will be described herein, a processor or controller may determine from the exercise data parameters such as initial burst (e.g., an athlete's "off the line" time, distance and/or speed). In one example, the initial burst measurement is a measurement of the time duration from an initial movement to an initial foot strike of a first step of a known exercise activity. In another example, metrics such as speed and distance of a user can be derived by determining a total number of steps taken by the user during the known exercise activity and the total time of performance of the known exercise activity. For example, a general multiplier can be applied (e.g., when each step is estimated for a known distance, thus multiplying the number of steps by the known distance to obtain the total distance performance during the known exercise activity). Thus, in general, an initial burst may be a time from a static position of the user and a first foot strike of the user, a time between subsequent foot strikes of a user, a distance traveled by the user during the known exercise activity, a speed of the user during the known exercise activity, etc.

Reference is now made to FIG. 1. FIG. 1 shows an example system 10 that includes a sensing device 105 and a receiver 110. The sensing device 105 has a sensor suite, shown at reference numeral 120, a processor, shown at reference numeral 125 and a transmitter/receiver unit, shown at reference numeral 130. Although not shown in FIG. 1, the sensor suite 120 of the sensing device 105 may have a heart rate monitor with capabilities to measure heart rate variability. The sensing device 105 is configured to exchange communications (e.g., data collected by the sensor suite 120 and aggregated by the processor 125) with the receiver 110. The receiver 110 is a computing device (also referred to as a "central computer") and has a processor unit 155 and a transmitter/receiver unit 160. The sensing device 105 sends data collected by the sensor suite 120 via its transmitter/receiver 130, and the central computer 110 receives the data from the sensing device 105 via its transmitter/receiver 160.

The sensor suite 120 of the sensing device 105 comprises one or more sensors that are configured to detect motions associated with an athlete (also referred to as a "user" herein) during performance of an athletic activity. For example, as shown in FIG. 1, the sensor suite 120 comprises an accelerometer sensor unit ("accelerometer") 135, a gyroscope sensor unit ("gyroscope") 140 and a magnetometer sensor unit ("magnetometer") 145. It should be appreciated that the accelerometer 135 may represent one or more accelerometers. For example, the accelerometer 135 may represent multiple single axis accelerometers. Alternatively, the accelerometer 135 may represent one or more multi-axis accelerometers (e.g., one or more tri-axial accelerometers). Similarly, the gyroscope 140 may represent one or more single axis gyroscopes or one or more multi-axis gyroscopes, and the magnetometer 145 may represent one or more single axis magnetometer or one or more multi-axis magnetometer. In one example, the accelerometer 135 is a tri-axial accelerometer, the gyroscope 140 is a tri-axial gyroscope and the magnetometer 145 is a tri-axial magnetometer. Thus, in this example, the sensor suite 120 may be configured as a multi-axis (nine-axis) sensor suite, configured to measure tri-axial acceleration of a user (e.g., magnitude and direction of an acceleration vector using the accelerometer 135), tri-axial angular rate of change of an athlete relative to the ground (using the gyroscope 140), and tri-axial heading measurements (using the magnetometer 145) thereby providing directional information relative to the ground.

The sensor suite 120 may include any additional sensors operable to track one or more parameters of the athlete and/or one or more biometric conditions of the athlete. By way of example, the sensing device 105 may include any movement sensor (such as a piezoelectric sensor) that produces voltage or current proportional to acceleration, mechanical stress or strain, etc. By way of further example, the sensing device 105 may further include a piezoelectric sensor operable to detect foot strikes. It should be appreciated that these are examples, and other sensors may be part of the sensor suite 120.

Figure 2:
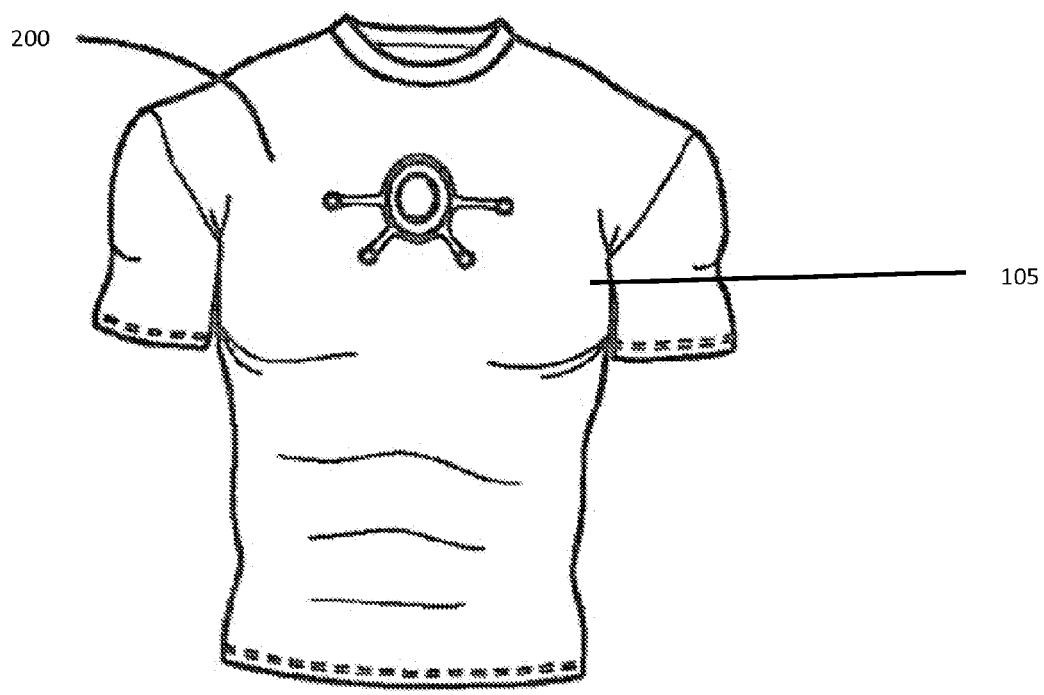
FIG. 2 illustrates the sensing device of FIG. 1, shown connected to an article of apparel to be worn over the torso.

As stated above, sensor suite 120 is configured to gather data of an athlete during performance of an athletic activity. The sensor suite 120 is also configured to gather data before performance of an athletic activity and after performance of an athletic activity. For example, as shown in FIG. 2, the sensor suite 120 may be part of an on-body sensing device 105 affixed to a shirt or other apparel (shown at reference numeral 200 in FIG. 2). In one example, the sensor suite 120 of the sensing device 105 is integrated in a shirt or other apparel of the athlete and measures performance characteristics of the athlete during a 40-yard dash exercise.

Each of the sensors (the accelerometer 135, the gyroscope 140 and the magnetometer 145) is configured to measure sensor data, and these sensors individually send the sensor data to the processor unit 125, as indicated by arrows 147(1)-147(3). It should be appreciated that other components of the sensor suite 120 not shown in FIG. 1 may send data to the processor unit 125 (e.g., movement sensors and/or piezoelectric sensors may send data to the sensor suite 120). The processor unit 125 has a sensor fusion module that receives the sensor data from each of the sensors of the sensor suite 120. The sensor fusion module 150 is configured to receive the sensor data from each of the sensors and is configured to unify ("aggregate" and/or "combine") the sensor data. In one example, the sensor fusion module 150 is a subroutine within the processor 125 that generates a unified representation of the parameters measured by one or more sensors in the sensor suite 120. The sensor fusion module 150 unifies the sensor data to create output data that may be utilized to calculate one or more metrics of athletic performance. In other words, the output data from the sensor fusion module 150 may be sent to the receiver 105 such that the central computer 110 can calculate one or more metrics of athletic performance. It should be appreciated that the sensor fusion module 150 may constitute hardware, software and/or firmware. In one example, the sensor fusion module 150 may comprise computer executable logic that causes the processor 125 to perform the data unification of the sensor data obtained by devices in the sensor suite 120.

As stated above, the components of the sensor suite 120 are configured to measure data of an athlete during performance of an athletic event. For example, when an athlete is participating in a 40-yard dash athletic event, the components of the sensor suite 120 are configured to measure exercise data of the athlete such as the athlete's initial burst (e.g., time "off the line" until a first foot strike), speed, distance, foot strike time, foot strike duration and numerosity, orientation, a user's stride length, a user's stride rate, airtime, etc.) It should be appreciated that though the examples described herein relate to measurements obtained during a 40-yard dash, the techniques are applicable to other athletic activities (such as other race events, track and field events, etc.), and in particular to any athletic activity where a user is moving from a static position to a moving position. For example, the techniques described herein may relate to measurement measurements or metrics (such as an initial burst, speed, distance, foot strike time, foot strike duration and numerocity, orientation, stride length, stride rate, airtime, etc.) for athletes performing American football related exercises. In one example, the techniques herein may relate to measurements for an athlete moving from a static position to a moving position (e.g., a player such as a receiver or lineman moving off the line of scrimmage after the ball is snapped, a player such as a running back, fullback, quarterback, kicker or defensive player moving after the ball is snapped, a player such as a kick returner moving after a ball is received, etc.).

Typically in a 40-yard dash, an athlete begins in a static or stationary position. The athlete is typically oriented at an angle with respect to a frame of reference (e.g., the ground). For example, an athlete in a starting position of a 40-yard dash may be positioned in a three point stance, where the torso of the athlete is bent at an angle from a vertical orientation. In one example, the athlete is bent at an angle of 100 degrees or more from a vertical orientation, though it should be appreciated that this is merely an example.

The present disclosure describes techniques for determining when the athlete is in a starting position for a known exercise activity (e.g., 40-yard dash). Upon a determination that the athlete is in a starting position for a 40-yard dash, the sensors in the sensor suite are armed (e.g., ready to gather data) for data collection associated with the athlete's participation in the 40-yard dash. In other words, once it is determined that the athlete is in a starting position for the 40-yard dash, the sensors in the sensor suite 120 are activated such that exercise data that is collected by the sensors soon after the arming is determined to be collected for a known exercise activity (i.e., the 40-yard dash). Thus, the sensing device 105 is said to be armed, meaning that when the sensing device 105 is armed, exercise data collected by the sensors in the sensor suite 120 and processed by the processor 125 is determined to be for a 40-yard dash. As described herein, the process of arming the sensing device 105 depends on a specific attitude/orientation and time threshold criteria that is specific to a known exercise activity. In one example, the determination of the athlete in the starting position is performed by the processor 125 of the sensing device 105.

Figure 3:
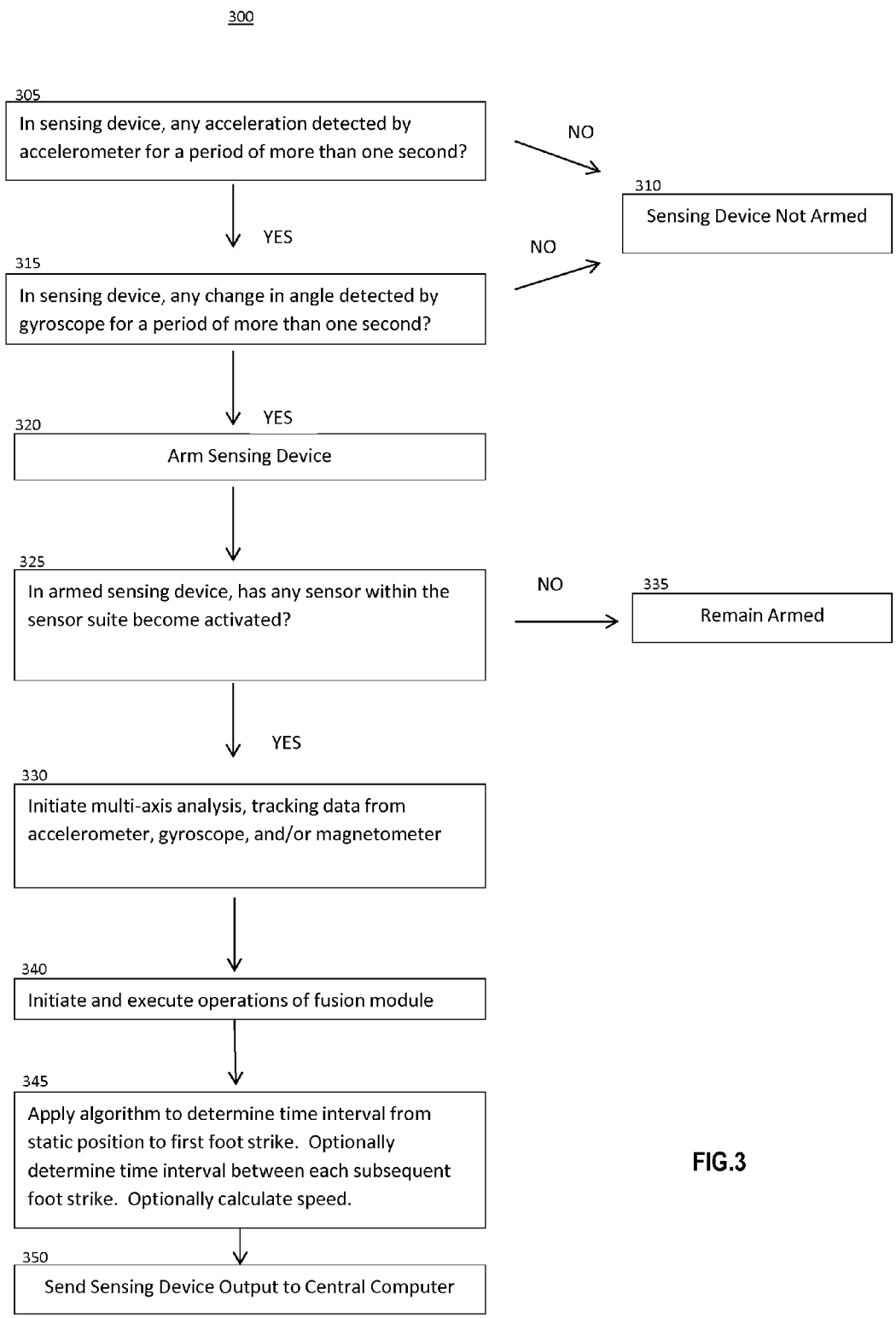
FIG. 3 is a flow diagram of the sensing device operation in accordance with an embodiment of the invention.

Reference is now made to FIG. 3, which shows a flowchart 300 of a process utilized by the processor 125 to determine whether or not the athlete is in a starting position. As shown in operation 305 in FIG. 3, the processor 125 determines whether or not any acceleration measurements have been detected or measured by the accelerometer 135 for a period of time greater than a predetermined time amount (e.g., a period of more than one second). In other words, the processor 125 determines a recency of an acceleration measurement. If an acceleration measurement was detected or measured by the accelerometer 135 for a period of time less than or equal to the predetermined time amount (e.g., less than or equal to one second), the processor 125 determines that the acceleration event is relatively recent, and the processor 125 does not arm the sensing device 105, as shown by operation 310 in FIG. 3. If, however, an acceleration measurement was detected or measured by the accelerometer 135 for a period of time greater than the predetermined time amount, the processor 125 determines that the acceleration event is not relatively recent (e.g., that the accelerometer has been inactive for at least the predetermined time amount). This may be indicative that the athlete has been in a static position, preparing to begin the 40-yard dash.

When the acceleration measurement, if any, was detected for a period of time greater than the predetermined time amount, the processor 125, at 315, determines whether or not any change in angle has been detected by the gyroscope 140 for a period of time greater than a predetermined time amount (e.g., a period of more than one second). Note that this predetermined time amount may be different from the predetermined time amount utilized to determine the recency of acceleration measurements. If a change in angle has been detected for a period of time greater than the predetermined time amount, the processor 125 determines that the change in angle is a recent event, and thus, the sensor device 105 is not armed. On the other hand, if the processor 125 determines that the change in angle is not a recent event (i.e., that the change in angle has been detected by the gyroscope 140 for a period of time less than or equal to the predetermined time amount), the processor 125 will arm the sensing device 105, as shown in operation 320 since the athlete is likely in the static starting position for the 40-yard dash. In an embodiment, the sensing device 105 becomes armed when the athlete is static and oriented at a predetermined attitude (called the normal position) for a predetermined period of time. As stated above, once the sensing device 105 is armed, data collected by the sensors in the sensor suite 120 and processed by the processor 125 is determined to be associated with the 40-yard dash undertaken by the athlete. In one example, the processor 125 determines and stores a time at which the arming occurs such that exercise data collected after the time at which the arming occurs is classified as being associated with the 40-yard dash. For example, exercise data collected after the time at which the arming occurs may be used to determine the initial burst value for the athlete.

Thus, in this example, the processor 125 will arm the sensor suite 120 when two conditions are met: (1) when an acceleration event measured by the acceleration sensor 135 is not relatively recent (e.g., if an acceleration was detected for a period longer than the predetermined time amount) and (2) when a change in angle measurement by the gyroscope 140 is not relatively recent (e.g., if a change in angle measurement is detected for a period longer than the predetermined time period). The processor 125 may drive software and/or firmware that is configured to arm the device when the athlete possesses an attitude falling within a predetermined range. By way of example, when measuring the athlete in a 40-yard dash, given the typical starting position of the athlete, the attitude may fall into a range of ±35° from horizontal. It should be understood, however, the predetermined attitude value may be selected to be any value, depending on the particular starting position of the athlete (i.e., it may be customized for a particular athlete's starting position). In yet another embodiment, the firmware may arm the device only when predetermined values for both the above mentioned inactivity and attitude parameters are simultaneously achieved. It should be appreciated that the predetermined time period may be any time period, and one second is used merely as an example.

There may be other examples, however, when the processor 125 will arm the sensor suite 120. For example, instead of determining a recency of acceleration and angular measurements, the processor 125 may determine whether not detected acceleration, angular measurements, directional measurements, etc. match predetermined expected values. If so, the sensor suite 120 may be armed. In other words, in the example above, the processor uses a predetermined time amount to determine recency of detected exercise data, and arms the sensor suite 120 only when the detected exercise data is not recent. Alternatively, the processor 125 may arm the sensor suite 120 when the exercise data matches a predetermined criteria, such as an expected motion position, acceleration value and/or directional position. In other words, the processor 125 may arm the sensor suite 120 when the exercise data matches a known movement pattern.

Referring back to FIG. 3, after the sensing device 105 is armed, the processor 125 determines whether or not any sensor in the sensor suite 120 is activated. This operation is shown at reference numeral 325 in FIG. 3. If any sensor in the sensor suite 120 is activated, the processor 125, at operation 330, will initiate a multi-axis analysis by receiving and tracking data from the accelerometer 135, gyroscope 140, magnetometer 145 and/or other components of the sensor suite 120. If none of the sensors in the sensor suite 120 is activated, the processor 125 will ensure that the sensing device 105 remains armed, as shown in operation 335.

After initiating the multi-axis analysis, the processor 125 will initiate the sensor fusion module 150, as shown at operation 340. As stated above, the sensor fusion module 150 is configured to generate a unified representation of the parameters measured by one or more sensors in the sensor suite 120. Upon initiating the sensor fusion module 150, the processor 125 applies an algorithm to determine a time interval between an athlete's static position to a first foot strike ("initial burst"). The algorithm may optionally determine a time interval between subsequent foot strikes and also the athlete's speed and distance as he or she performs the 40-yard dash. Upon calculating these metrics, the sensing device 105 can output or send the metrics to the central computer 110, as described in operation 350. In one example, the processor 125 is configured to calculate a time of a first foot strike during the 40-yard dash, a time between a first foot strike and a second foot strike, a second foot strike and a third foot strike, and so on. In another example, the processor 125 is configured to calculate data such as the initial speed of the athlete, the running speed of the athlete, and/or the distance covered by the athlete. Once collected and calculated, the sensing device 105 sends selected data to the central computer 110. Optionally, the central computer 110 may receive the unified data from the sensing device 105, and the processor 155 of the central computer 110 may determine the characteristics described above.

It should be appreciated that the processor 125 may be configured to determine that some or all data collected after the sensing device 105 is armed may not be associated with the known exercise activity. For example, the processor 125 may determine that some or all of the data measured by the sensor suite 120 is not associated with the known exercise activity (40 yard dash) and/or with a metric desired for the known exercise activity (initial burst). In one example, if the sensing device 105 is armed, but the processor 125 determines that a first step of a user occurred too quickly or too slowly (e.g., based known reaction times for human movement), the processor 125 may disregard a portion of the data collected from the sensor suite 120. In this example, the processor 125 may then determine another arming instance of the sensing device 105.

In one example, the transmitter/receiver ("transceiver") 130 of the sensing device 105 is operable to wirelessly communicate with other devices such as the central computer 110 via any wireless protocol suitable for its described purpose. A representation of wireless communication capabilities is shown at reference numeral 170 in FIG. 1. Additionally, the transmitter/receiver 130 may communicate with mobile devices (smartphones, etc.). The transmitter/receiver 160 of the central computer 110 is configured to receive data from the transmitter/receiver 130 of the sensing device 105. In one example, the central computer 110 may display the data to the athlete or send/store the data to a server or database accessible by the athlete, coach or other interested party.

Thus, the system 10 described above is configured to detect movement of an athlete from a static or stationary position by tracking core body movement on a plurality of axes. The system 10 is configured to measure the first step of an athlete, i.e., the time interval from the static position (which is a known, or normal, position) to the first foot strike (i.e., the ground contact of the first step). Additionally, the system 10 may be configured to track the time interval between the first foot strike and the second foot strike, the second foot strike and the third foot strike, and so forth. In further embodiments, the sensing device 105 is configured to count foot strikes. With this configuration, the sensing device 105 is capable of tracking the acceleration of the athlete from the static position and, if desired, of collecting data for any predetermined period of time and/or number of foot strikes. The system 10 is particularly useful in tracking the performance of an athlete in an activity such as a football receiver beginning a route, a 40-yard dash, or any other running activity of short duration.

The above system including the nine-axis sensor enables an operator to track not only an athlete's first step, but also to compare any number of foot strikes (any selected collection of foot strikes) during the run. Thus, it possible not only to determine an athlete's "off the line" quickness (time between the initial core body movement, to ground contact of first foot), but also the time passage between each and every foot strike. The system enables the measurement regardless of the size, weight, or form of the particular athlete. This assists the athlete in identifying areas of improvement—improving initial speed (the first step), maintaining speed throughout a run, or maintaining speed through a predetermined distance.

While the invention has been described in detail and with reference to specific embodiments thereof, it will be apparent to one skilled in the art that various changes and modifications can be made therein without departing from the spirit and scope thereof. It is to be understood that terms such as "top," "bottom," "front," "rear," "side," "height," "length," "width," "upper," "lower," "interior," "exterior," "medial," "lateral," and the like as may be used herein, merely describe points of reference and do not limit the present invention to any particular orientation or configuration. For example, sensing, in general, refers to sensors taking some measurements of a parameter.

The sensing device 105 may include any kinematic and/or kinetic sensors suitable for its described purpose The sensing device 105 may automatically transmit data in real-time, i.e., at the same time the athlete participates in the sporting event. In one embodiment, the sensing device 105 transmits data immediately upon receipt of a signal from the sensor worn by the athlete. However, in other embodiments, the sensing device 105 may be configured to conserve power by only transmitting data in a periodic fashion, such as once every second, once every ten seconds, once every thirty seconds, etc. In these embodiments, the electronics package for the sensing device 105 may include a memory configured to store a limited amount of data taken over a short period of time and then transmit that data and associated time information in a single transmission. In any event, the system is configured to regularly and automatically transmit data as the athlete participates in the sporting event.

The wireless transmission may utilize any known or future network types. For example, the wireless telephony network may comprise commonly used cellular phone networks using CDMA or FDMA communications schemes. Some other examples of currently known wireless telephony networks include Wi-Fi, WiMax, GSM networks, and BLUETOOTH, as well as various other current or future wireless telecommunications arrangements.

The sensing device 105 output is transmitted to the central computer 110, which may include or be in communication with processing servers. In an embodiment, the processing servers are remotely located from the sporting venue where the athlete is participating in the sporting event. The processing server may comprise a single Internet server, or a server connected to other computers that perform processing and data storage functions. In at least one alternative embodiment, the processing server may be located at the sporting venue where the athlete is participating in the sporting event. For example, the processing server could be located within the same stadium where an athlete is participating.

The types of calculations performed by the sensing device 105 and or the central computer 110 are not particularly limited. These components may perform various calculations on the data and also process the data into any of various forms. Typical calculations performed by the computer might relate to the athlete's current performance, improvement, history, training state, etc.

Foot strikes may be identified utilizing any suitable manner. For example, amplitudes on a vector graph falling within a specified time window may be utilized to identify foot strikes. In an embodiment, the sensor suite measurements may be utilized to indicate when a portion of (e.g., the rear portion) or the entire foot is raised from the ground, as well as when a portion of or the entire foot contacts the ground through the identification of specific amplitude indications on the graph. In other embodiments, a sensor (e.g., piezoelectric sensor) may be utilized to identify foot strikes).

The sensor-fusion module enables reconstruction via sensor-fusion techniques/algorithms of the global state of the athlete being monitored. Various fusion algorithms may be applied for fusing sensor data, including but not limited to Kalman filter algorithm, Bayesian networks algorithm, and Dempster-Shafer algorithm. The fusion of parameters may generate a fused or output parameter consisting of each of measured sensor parameter. The sensor fusion module may be configured to weight a sensor signal by its associated confidence value, and may disregard a sensor value (excluding it from fusion) if it falls outside of a predetermined range. By way of example, the fusion module may consolidate position, movement, attitude signals from the sensor suite to determine athlete location and/or orientation (foot strike, etc.) based on, inter alia, the acceleration magnitude and direction of movement.

The algorithm automatically identifies the 40-yard dash start, and record step time, and is refined to remove instances of false positive or false negative data. Additionally, the algorithm may be configured to instantaneously report step times wirelessly back to the central computer or other receiver. The foot strikes may be measured in milliseconds, and reported instantaneously to UA local receiver. This receiver may further be connected directly or indirectly to other receivers, e.g., television production receivers, so that the data may be displayed on air.

Figure 4:
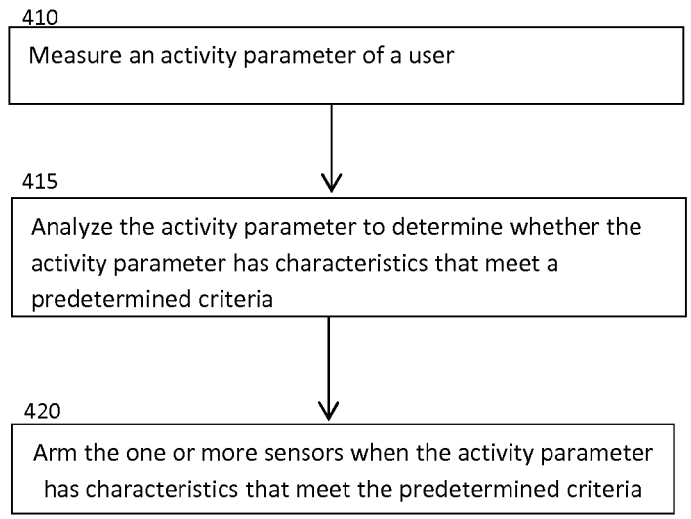
FIG. 4 is a flow diagram of the sensing device operation for arming one or more sensors.

Reference is now made to FIG. 4, which shows an example flow chart 400 depicting operations for arming the one or more sensors in the sensor suite 120. At operation 410, a processor (e.g., processor 125) measures an activity parameter of a user (e.g., data from the accelerometer 135, gyroscope 140, and/or magnetometer 145). At 415, the processor analyzes the activity parameter to determine whether the activity parameter has characteristics that meet a predetermined criteria (e.g., whether the activity parameter was detected after a predetermined amount of time). At 420, the processor arms the one or more sensors when the activity parameter has characteristics that meeting the predetermined criteria. The arming comprises activating the one or more sensors to collect exercise data for a known exercise activity (e.g., a 40-yard dash) performed by the user.

Reference is now made to FIG. 5, which shows an example flow chart 500 for collecting exercise data for a user. At reference numeral 510, the processor 125 arms the one or more sensors to collect data when an activity parameter of a user meets a predetermined criteria. At 515, the processor collects exercise data for a known exercise activity performed by the user.

Figure 6:
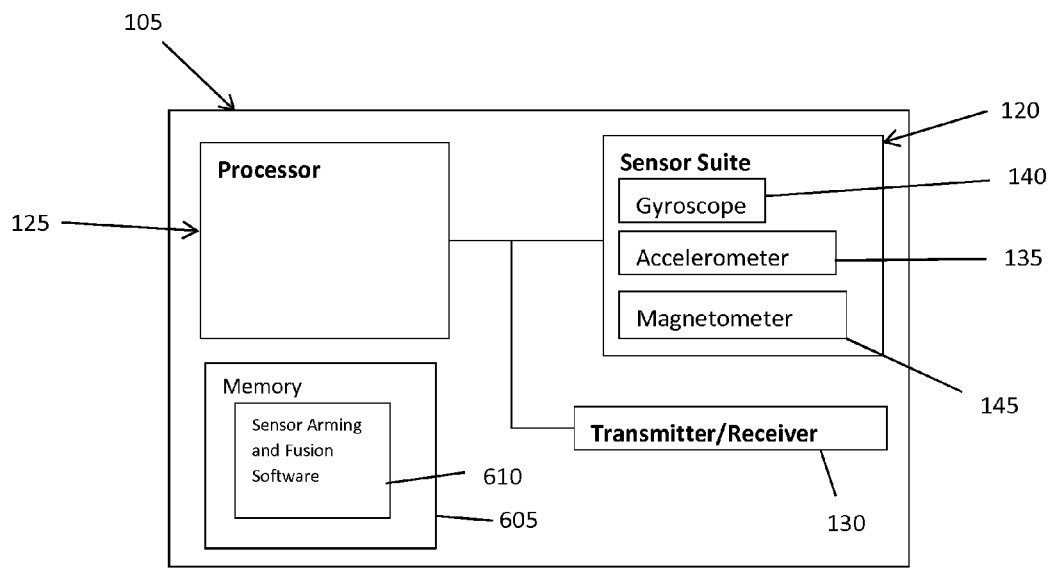
FIG. 6 is a block diagram of sensing device configured to arm and collect exercise data.

Reference is now made to FIG. 6. FIG. 6 shows an example block diagram 105 of the sensing device. The sensing device 105 has the processor 125, the sensor suite 120, the transmitter/receiver 130 and a memory 605. The sensor suite 120 comprises a plurality of sensor devices, including for example, the accelerometer 135, the gyroscope 140 and the magnetometer 145. The sensor suite 120 and the transmitter/receiver 130 are coupled to or in communication with the processor 125. The processor 125 is, for example, a microprocessor or microcontroller that is configured to execute program logic instructions (i.e., software) for carrying out various operations and tasks of the sensing device 105, as described above. For example, the processor 125 is configured to sensor arming fusion software 610 to arm the sensors and to detect unify sensor data obtained from components of the sensor suite 120, as described by the techniques above. The functions of the processor 125 may be implemented by logic encoded in one or more tangible computer readable storage media or devices (e.g., storage devices, compact discs, digital video discs, flash memory drives, etc. and embedded logic such as an application specific integrated circuit, digital signal processor instructions, software that is executed by a processor, etc.).

The memory 605 may comprise read only memory (ROM), random access memory (RAM), magnetic disk storage media devices, optical storage media devices, flash memory devices, electrical, optical, or other physical/tangible (non-transitory) memory storage devices. The memory 605 stores software instructions for the sensor arming and fusion software 610. Thus, in general, the memory 605 may comprise one or more computer readable storage media (e.g., a memory storage device) encoded with software comprising computer executable instructions and when the software is executed (e.g., by the processor 125) it is operable to perform the operations described for the sensor arming and fusion software 610, as described herein.

The sensor arming and fusion software 610 may take any of a variety of forms, so as to be encoded in one or more tangible computer readable memory media or storage device for execution, such as fixed logic or programmable logic (e.g., software/computer instructions executed by a processor), and the processor 125 may be an ASIC that comprises fixed digital logic or a combination thereof.

For example, the processor 125 may be embodied by digital logic gates in a fixed or programmable digital logic integrated circuit, which digital logic gates are configured to perform the sensor arming and fusion software 610. In general the sensor arming and fusion software 610 may be embodied in one or more computer readable storage media encoded with software comprising computer executable instructions and when the software is executed operable to perform the operations described herein.

Thus, it is intended that the present invention covers the modifications and variations of this invention provided they come within the scope of the appended claims and their equivalents. It should be appreciated that the techniques described above in connection with all embodiments may be performed by one or more computer readable storage media that is encoded with software comprising computer executable instructions to perform the methods and steps described herein. For example, the operations performed by the sensing device 105 and the central computer 110 may be performed by one or more computer or machine readable storage media (non-transitory) or device executed by a processor and comprising software, hardware or a combination of software and hardware to perform the techniques described herein.

In summary, a method for obtaining athletic data is provided comprising: at a processor, measuring an activity parameter of a user; analyzing the activity parameter to determine whether the activity parameter has characteristics that meet a predetermined criteria; and arming the one or more sensors when the activity parameter has characteristics that meet the predetermined criteria, wherein the arming comprises activating the one or more sensors to collect exercise data for a known exercise activity performed by the user.

In addition, a method for obtaining athletic data is provided comprising: at a processor, arming the one or more sensors to collect data when an activity parameter of a user meets a predetermined criteria; and after arming the one or more sensors, collecting exercise data for a known exercise activity performed by the user.

Furthermore, an apparatus is provided comprising: a sensor suite unit comprising one or more sensors that measure an activity parameter of a user; and a processor in communication with the sensor suite and configured to: analyze the activity parameter to determine whether the activity parameter has characteristics that meet a predetermined criteria; and arm the one or more sensors when the activity parameter has characteristics that meet the predetermined criteria to collect exercise data for a known exercise activity performed by the user.

The above description is intended by way of example only. Various modifications and structural changes may be made therein without departing from the scope of the concepts described herein and within the scope and range of equivalents of the claims.

What is claimed is:

1. A method for obtaining athletic data, the method comprising:
    at a processor, measuring a body position and acceleration of a user;
    analyzing the body position to determine whether predetermined criteria indicative of a known exercise activity are met;
    arming one or more sensors when the body position has not substantially changed and the acceleration of the user has remained at zero for a predetermined period of time, wherein the arming comprises activating the one or more sensors to collect exercise data;
    determining a time at which the one or more sensors are armed;
    after the time at which the one or more sensors are armed, collecting the exercise data, during a first time period associated with substantially no acceleration and no change in orientation of the user and during a second time period associated with a first acceleration and a change in orientation of the user;
    analyzing the exercise data to determine whether the data collected during the second time period corresponds to the known exercise activity; and
    when it is determined that the data collected during the second time period corresponds to the known exercise activity:
        calculating an initial burst by determining a difference between the first and second times; and
        enabling display of the calculation.

2. The method of claim 1, further comprising when it is determined that the data collected during the second time period corresponds to the known exercise activity,
    classifying the exercise data collected during the second time period as data associated with the known exercise activity performed by the user.

3. The method of claim 2, wherein classifying comprises classifying the collected exercise data as data associated with a 40-yard dash performed by the user.

4. The method of claim 1, wherein the initial burst value further comprises determining a time between an initial core body movement of the user and a time of first ground contact by a foot of the user.

5. The method of claim 1, further comprising when it is determined that the data collected during the second time period corresponds to the known exercise activity, classifying the collected exercise data over a time range that includes a time prior to the time at which the arming occurs, the first time period and the second time period.

6. The method of claim 1, wherein:
    the determination that the acceleration of the user has remained at zero for a predetermined period of time comprises measuring an inactivity time via one or more acceleration sensors; and
    the determination that the body position of the user has not substantially changed for a predetermined period of time comprises utilization of at one or more gyroscopes.

7. The method of claim 1, wherein:
    measuring the body position comprises measuring an orientation of the one or more sensors coupled to the user with respect to a frame of reference; and
    arming comprises arming the one or more sensors when an angle of orientation of the user relative to the frame of reference does not vary outside of a predetermined acceptable range.

8. The method of claim 7, wherein measuring the orientation of the user comprises measuring an attitude of the one or more sensors coupled to the user relative to a horizontal orientation.

9. A method for obtaining athletic data, the method comprising:
    receiving data indicating that acceleration of the user measured at one or more sensors has remained zero for a predetermined period of time;
    receiving data indicating that an orientation of the user measured at one or more sensors has not changed for the predetermined period of time;
    at a processor of a sensing device, arming the one or more sensors to collect data;
    determining a time at which the arming occurred;
    after the time at which the arming occurs, collecting; and
    determining whether the collected exercise data corresponds to a known exercise activity;
    when it is determined that the collected exercise data does not correspond to a known exercise activity, restarting a timer for the determination that the acceleration of the user has remained zero for a predetermined period of time and the orientation of the user has not changed for the predetermined period of time; and
    when it is determined that the collected exercise data corresponds to a known exercise activity, unifying the collected exercise data for transmission to a computing device.

10. The method of claim 9, further comprising determining an initial burst value by determining a time between an initial core body movement of the user and a time of first ground contact by a foot of the user.

11. The method of claim 9, further comprising:
    determining from the exercise data one of a time from a static position of the user to a first foot strike of the user performed during the known exercise activity, a time between subsequent foot strikes of the user performed during the known exercise activity, a distance traveled by the user during the known exercise activity or a speed of the user during the known exercise activity.

12. An apparatus for obtaining athletic data, the apparatus comprising:
    a sensor suite unit comprising one or more sensors that measure an activity parameter of a user; and
    a processor in communication with the sensor suite and configured to:
        analyze the activity parameter to determine whether the user is static and orientated at a predetermined attitude for a predetermined period of time;
        arm the sensor suite when it is determined that the user is static and orientated at the predetermined attitude for the predetermined period of time, wherein the armed sensor suite is configured to collect exercise data;
        determine a time at which the sensor suite is armed;
        analyze the collected exercise data to determine whether the exercise data collected after the sensor suite is armed corresponds to a known exercise activity performed by the user; and when it is determined that the exercise data collected after the sensor suite is armed does not correspond to a known exercise activity, disregard the exercise data.

13. The apparatus of claim 12, wherein the processor is further configured to: when it is determined that the exercise data collected after the sensor suite is armed corresponds to a known exercise activity, classify the collected exercise data as data associated with the known exercise activity performed by the user.

14. The apparatus of claim 13, wherein the processor is further configured to classify the collected exercise data as data associated with a 40-yard dash performed by the user.

15. The apparatus of claim 12, wherein the processor is further configured to when it is determined that the exercise data collected after the sensor suite is armed corresponds to a known exercise activity, determine based at least in part on the collected exercise data an initial burst value for the user.

16. The method of claim 9, wherein the one or more sensors comprise one or more of: an accelerometer, a gyroscope and a magnetometer.

17. The method of claim 9, wherein the one or more sensors includes at least a nine-axis sensor configured to track the user's first step and compare a collection of sensed foot strikes to enable identification of areas for improvement.

18. The apparatus of claim 12, wherein the sensor suite comprises one or more of:
an accelerometer,
a gyroscope,
a magnetometer,
a nine-axis sensor configured to track the user's first step and compare a collection of sensed foot strikes to enable identification of areas for improvement.

19. The method of claim 1, wherein when it is determined that the data collected during the second time period does not correspond to the known exercise activity, disregarding the exercise data.

20. The method of claim 9, wherein when it is determined that the collected exercise data does not correspond to a known exercise activity, disregarding the exercise data.

21. The apparatus of claim 12, wherein the processor is further configured to: when it is determined that the exercise data collected after the sensor suite is armed does not correspond to a known exercise activity, restart a timer for the analysis of the activity parameter to determine whether the user is static and orientated at a predetermined attitude for a predetermined period of time.

* * * * *